(12) United States Patent
Yun et al.

(10) Patent No.: US 9,109,237 B2
(45) Date of Patent: Aug. 18, 2015

(54) METHOD OF PREPARING PICEATANNOL USING BACTERIAL CYTOCHROME P450 AND COMPOSITION THEREFOR

(71) Applicant: Chul Ho Yun, Daejeon (KR)

(72) Inventors: Chul Ho Yun, Daejeon (KR); Dong Hyun Kim, Chungcheongnam-Do (KR)

(73) Assignee: Chul Ho Yun, Daejeon (KR)

( * ) Notice: Subject to any disclaimer, the term of this patent is extended or adjusted under 35 U.S.C. 154(b) by 59 days.

(21) Appl. No.: 14/041,403

(22) Filed: Sep. 30, 2013

(65) Prior Publication Data

US 2014/0106423 A1 Apr. 17, 2014

Related U.S. Application Data

(60) Division of application No. 13/132,420, which is a continuation of application No. PCT/KR2009/001859, filed on Apr. 10, 2009, now abandoned.

(30) Foreign Application Priority Data

Dec. 3, 2008 (KR) .................. 10-2008-0122029

(51) Int. Cl.
*C12P 7/22* (2006.01)
*C12N 9/02* (2006.01)

(52) U.S. Cl.
CPC .............. *C12P 7/22* (2013.01); *C12N 9/0071* (2013.01); *C12Y 114/14001* (2013.01)

(58) Field of Classification Search
CPC .................. C12N 9/0071; C12Y 114/14001; C12P 7/22; C12P 17/06
See application file for complete search history.

(56) References Cited

U.S. PATENT DOCUMENTS 7,531,335 B1 5/2009 Hauer et al.
2010/0267083 A1 10/2010 Hauer et al.

FOREIGN PATENT DOCUMENTS

| KR | 10-2007-0066104 | 6/2007 |
| KR | 10-2008-0063005 | 7/2008 |
| WO | WO 01/07574 | 2/2001 |
| WO | WO 2005/042748 | 5/2005 |
| WO | WO 2008/012321 | 1/2008 |
| WO | WO 2008/016709 | 2/2008 |
| WO | WO 2008/098198 | 8/2008 |
| WO | WO 2008/121435 | 10/2008 |

OTHER PUBLICATIONS

Kim et al., Drug Metabolism and Disposition 36(11):2166-2170, available online Jul. 31, 2008.*

Athar M, Back JH, Tang X, Kim KH, Kopelovich L, Bickers DR, Kim AL (2007) Resveratrol: a review of preclinical studies for human cancer prevention. *Toxicol Appl Pharmaco*. 224:274-283.
Bernhardt R (2006) Cytochromes P450 as versatile biocatalysts. *J Biotechnol* 124:128-145.
Branden et al. (1991) *Introduction to Protein Structure*. Garland Publishing Inc. New York. p. 247.
Carmichael AB and Wong LL (2001) Protein engineering of *Bacillus megaterium* CYP102. The oxidation of polycyclic aromatic hydrocarbons. *Eur J Biochem* 268:3117-3125.
Chun YJ, Kim S, Kim D, Lee SK, Guengerich FP. (2001) A new selective and potent inhibitor of human cytochrome P450 1B1 and its application to antimutagenesis. *Cancer Res* 61:8164-8170.
Chun YJ, Kim MY, Guengerich FP. (1999) Resveratrol is a selective human cytochrome P450 1A1 inhibitor. *Biochem Biophys Res Commun* 262:20-24.
Damsten et al. (2008), "Application of drug metabolizing mutants of cytochrome P450 BM3 (CYP102A1) as biocatalysts for the generation of reactive metabolites," *Chemico-Biological Interactions*, 171(1), pp. 96-107.
Di Nardo G, Fantuzzi A, Sideri A, Panicco P, Sassone C, Giunta C and Gilardi G (2007) Wild-type CYP102A1 as a biocatalyst: turnover of drugs usually metabolised by human liver enzymes. *J Biol Inorg Chem* 12:313-323.
Farinas ET, Schwaneberg U, Glieder A and Arnold FH (2001) Directed evolution of a cytochrome P450 monooxygenase for alkane oxidation. *Advanced Synthesis & Catalysis* 343:601-606.
Fairman DA, Collins C, Chapple S (2007) Progress curve analysis of CYP1A2 inhibition: a more informative approach to the assessment of mechanism-based inactivation *Drug Metab Dispos* 35:2159-2165.
Guengerich FP (2002) Cytochrome P450 enzymes in the generation of commercial products. *Nat Rev Drug Discov* 1:359-366.
Guengerich FP, Gillam EM, Shimada T (1996) New applications of bacterial systems to problems in toxicology. *Crit Rev Toxicol* 26: 551-583.
Johnson MD, Zuo H, Lee K, Trebley JP, Rae JM, Weatherman RV, Zeruesanay D, Flockhart DA, Skaar TC (2004) Pharmacological characterization of 4-hydroxy-N-desmethyl tamoxifen, a novel metabolite of tamoxifen. *Breast Cancer Res Treat* 207:1-9.
Kim DH, Kim KH, Isin EM, Guengerich FP, Chae HZ, Ahn T, Yun CH. (2008c) Heterologous expression and characterization of wild-type human cytochrome P450 1A2 without conventional N-terminal modification in *Escherichia coli*. Protein Expr Purif. 57:188-200.
Kim DH, Kim KH, Kim DH, Liu KH, Jung HC, Pan JG, Yun CH (2008a) Generation of human metabolites of 7-ethoxycoumarin by bacterial cytochrome P450 BM3. *Drug Metab Dispos* 36:2166-2170.
Kim et al. (2009), "Generation of the Human Metabolite Piceatannol from the Anticancer-Preventive Agent Resveratrol by Bacterial Cytochrome P450 BM3," *Drug Metabolism and Disposition*, 37(5), pp. 932-936.
Kim YH, Kwon HS, Kim DH, Cho HJ, Lee HS, Jun JG, Park JH, Kim JK (2008b) Piceatannol, a stilbene present in grapes, attenuates dextran sulfate sodium-induced colitis. *Int Immunopharmacol* 8:1695-1702.

(Continued)

*Primary Examiner* — Delia Ramirez
(74) *Attorney, Agent, or Firm* — Lathrop & Gage LLP

(57) ABSTRACT

Provided is a method of preparing piceatannol, and more particularly, to a method of preparing piceatannol from resveratrol using bacterial cytochrome P450 BM3 (CYP102A1) or mutants thereof, and a composition and a kit therefor.

15 Claims, 6 Drawing Sheets

(56) References Cited

OTHER PUBLICATIONS

Kundu JK, Surh YJ (2008) Cancer chemopreventive and therapeutic potential of resveratrol: mechanistic perspectives. *Cancer Lett* 269:243-261.

Lamb DC, Waterman MR, Kelly SL and Guengerich FP (2007) Cytochromes P450 and drug discovery. *Curr Opin Biotechnol* 18:504-512.

Li QS, Ogawa J, Schmid RD and Shimizu S (2001) Engineering cytochrome P450.

BM-3 for oxidation of polycyclic aromatic hydrocarbons. *Appl Environ Microbiol* 67:5735-5739.

Mikstacka R, Rimando AM, Szalaty K, Stasik K, Baer-Dubowska W (2006) Effect of natural analogues of *trans*-resveratrol on cytochromes P4501A2 and 2E1 catalytic activities. *Xenobiotica* 36:269-285.

Narhi LO and Fulco AJ (1982) Phenobarbital induction of a soluble cytochrome P-450-dependent fatty acid monooxygenase in *Bacillus megaterium*. *J. Biol. Chem.* 257:2147-150.

Omura T and Sato R (1964) The carbon monoxide-binding pigment of liver microsomes. II. Solubilization, purification, and properties. *J Biol Chem* 239:2379-2385.

Otey CR, Bandara G, Lalonde J, Takahashi K and Arnold FH (2005) Preparation of human metabolites of propranolol using laboratory-evolved bacterial cytochrome P450. *Biotechnol Bioeng* 93:494-499.

Parikh A, Gillam EM, Guengerich FP (1997) Drug metabolism by *Escherichia coli* expressing human cytochromes P450. *Nat Biotechnol* 15:784-788.

Parikh A. et al. 'Selection and characterization of human cytochrome P450 1A2 mutants with altered catalytic properties.' In: Biochemistry. Apr. 1999, vol. 38(17), pp. 5283-5289.

Pirola L, Frojdo (2008) Resveratrol: one molecule, many targets. *IUBMB Life* 60:323-332.

Potter GA, Patterson LH, Wanogho E, Perry PJ, Butler PC, Ijaz T, Ruparelia KC, Lamb JH, Farmer PB, Stanley LA, Burke MD (2002) The cancer preventative agent resveratrol is converted to the anticancer agent piceatannol by the cytochrome P450 enzyme CYP1B1. *Br J Cancer* 86:774-778.

Piver B, Fer M, Vitrac X, Merillon JM, Dreano Y, Berthou F, Lucas D. (2004) Involvement of cytochrome P450 1A2 in the biotransformation of *trans*-resveratrol in human liver microsomes. *Biochem Pharmacol* 68:773-782.

Rushmore TH, Reider PJ, Slaughter D, Assang C, Shou M (2000) Bioreactor systems in drug metabolism: Synthesis of cytochrome P450-generated metabolites. *Metab Eng* 2:115-125.

Seffernick et al. (2001) "Melamine Deaminase and Atrazine Chlorohydrolase: 98 Percent Identical but Functionally Different," *J. Bacteriol.* 183(8):2405-2410.

Stottmeister U, Aurich A, Wilde H, Andersch J, Schmidt S, Sicker D (2005) White biotechnology for green chemistry: fermentative 2-oxocarboxylic acids as novel building blocks for subsequent chemical syntheses. *J Ind Microbiol Biotechnol* 32:651-664.

Supplementary European Search Report corresponding to European Application No. EP09830502.2, issued Jan. 11, 2013 (7 pages).

Urlacher VB and Eiben S (2006) Cytochrome P450 monooxygenases: perspectives for synthetic application. *Trends Biotechnol* 24:324-330.

Vail RB, Homann MJ, Hanna I, Zaks A (2005) Preparative synthesis of drug metabolites using human cytochrome P450s 3A4, 2C9 and 1A2 with NADPH-P450 reductase expressed in *Escherichia coli*. *J Ind Microbiol Biotechnol* 32:67-74.

van Vugt-Lussenburg BM, Damsten MC, Maasdijk DM, Vermeulen NP and Commandeur JN (2006) Heterotropic and homotropic cooperativity by a drug-metabolizing mutant of cytochrome P450 BM3. *Biochem Biophys Res Commun* 346:810-818.

van Vugt-Lussenburg BM, Stjernschantz E, Lastdrager J, Oostenbrink C, Vermeulen NP and Commandeur JN (2007) Identification of critical residues in novel drug-metabolizing mutants of cytochrome P450 BM3 using random mutagenesis. *J Med Chem* 50:455-461.

Witkowski et al. (1999) "Conversion of a β-Ketoacyl Synthase to a Malonyl Decarboxylase by Replacement of the Active-Site Cysteine with Glutamine," *Biochemistry*. 38:11643-11650.

Yun CH, Kim KH, Kim DH, Jung HC and Pan JG (2007) The bacterial P450 BM3: a prototype for a biocatalyst with human P450 activities. *Trends Biotechnol* 25:289-298.

\* cited by examiner

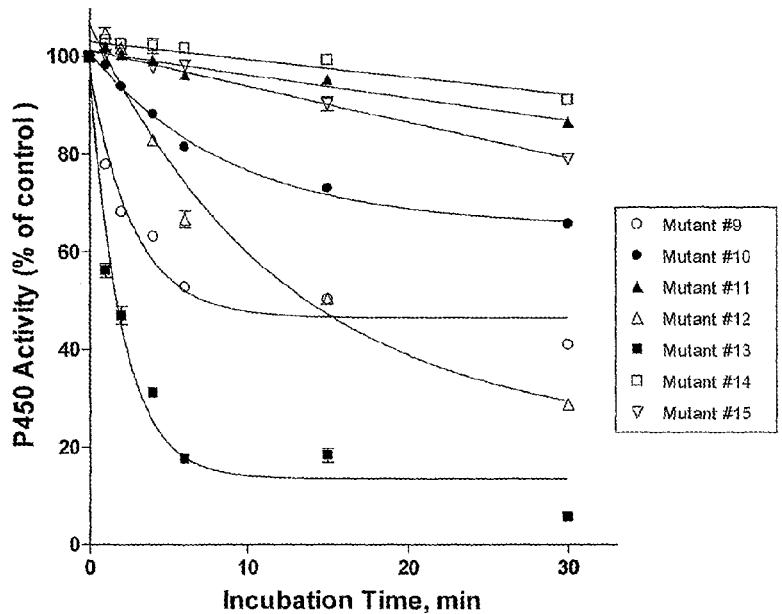

Figure 6 amino acid sequence of CYP102A1

```
TIKEMPQPKTFGELKNLPLLNTDKPVQALMKIADELGEIFKFEAPGRVTRYLSSQRLIKEACDE
SRFDKNLSQALKFVRDFAGDGLFTSWTHEKNWKKAHNILLPSFSQQAMKGYHAMMVDIAVQLVQ
KWERLNADEHIEVPEDMTRLTLDTIGLCGFNYRFNSFYRDQPHPFITSMVRALDEAMNKLQRAN
PDDPAYDENKRQFQEDIKVMNDLVDKIIADRKASGEQSDDLLTHMLNGKDPETGEPLDDENIRY
QIITFLIAGHETTSGILSFALYFLVKNPHVLQKAAEEAARVLVDPVPSYKQVKQLKYVGMVLNE
ALRLWPTAPAFSLYAKEDTVLGGEYPLEKGDELMVLIPQLHRDKTIWGDDVEEFRPERFENPSA
IPQHAFKPFGNGQRACIGQQFALHEATLVLGMMLKHFDFEDHTNYELDIKETLTLKPEGFVVKA
KSKKIPLGGIPSPSTEQSAKKVRKKAENAHNTPLLVLYGSNMGTAEGTARDLADIAMSKGFAPQ
VATLDSHAGNLPREGAVLIVTASYNGHPPDNAKQFVDWLDQASADEVKGVRYSVFGCGDKNWAT
TYQKVPAFIDETLAAKGAENIADRGEADASDDFEGTYEEWREHMWSDVAAYFNLDIENSEDNKS
TLSLQFVDSAADMPLAKMHGAFSTNVVASKELQQPGSARSTRHLEIELPKEASYQEGDHLGVIP
RNYEGIVNRVTARFGLDASQQIRLEAEEEKLAHLPLAKTVSVEELLQYVELQDPVTRTQLRAMA
AKTVCPPHKVELEALLEKQAYKEQVLAKRLTMLELLEKYPACEMKFSEFIALLPSIRPRYYSIS
SSPRVDEKQASITVSVVSGEAWSGYGEYKGIASNYLAELQEGDTITCFISTPQSEFTLPKDPET
PLIMVGPGTGVAPFRGFVQARKQLKEQGQSLGEAHLYFGCRSPHEDYLYQEELFNAQSEGIITL
HTAFSRMPNQPKTYVQHVMEQDGKKLIELLDQGAHFYICGDGSQMAPAVEATLMKSYADVHQVS
EADARLWLQQLEEKGRYAKDVWAG-
```

Figure 7

METHOD OF PREPARING PICEATANNOL USING BACTERIAL CYTOCHROME P450 AND COMPOSITION THEREFOR

CROSS-REFERENCE TO RELATED APPLICATIONS

This application is a divisional of U.S. patent application Ser. No. 13/132,420 (now abandoned), having a 371(c) date of Jun. 2, 2011, which is the U.S. national stage application under 35 U.S.C. §371 of International Application No. PCT/KR2009/001859, filed Apr. 10, 2009, which claims the benefit of Korean Application No. 10-2008-0122029 filed Dec. 3, 2008, each of which is hereby incorporated by reference to the extent it is not inconsistent with the present disclosure.

REFERENCE TO A SEQUENCE LISTING

A sequence listing containing SEQ ID NOs:1-16 is submitted herewith and is specifically incorporated by reference.

TECHNICAL FIELD

The present invention relates to a method of preparing expensive piceatannol from resveratrol using bacterial cytochrome P450 BM3 (CYP102A1) or mutants thereof.

This work was supported in part by the 21C Frontier Microbial Genomics and Application Center Program of the Ministry of Education, Science & Technology of the Republic of Korea [Project No.: MG08-0306-2-0, Title: Development of humanized bacterial monooxygenase for fine chemicals using microbial cytochrome P450 enzyme genomics].

BACKGROUND ART

Resveratrol (3,4',5-trihydroxystilbene) is a phytoalexin, which is an antitoxic substance produced by a plant tissue in response to external toxicity and found in a wide variety of dietary sources including grapes, plums, and peanuts. It exhibits beneficial effects including anti-oxidant, anti-inflammatory, cardioprotective, and anti-tumor activities (Kundu and Surh, 2008; Pirola and Fröjdö, 2008; Athar, et al., 2007). Currently, numerous preclinical findings suggest resveratrol as a promising nature's arsenal for cancer prevention and treatment. As a potential anti-cancer agent, resveratrol has been shown to inhibit or retard the growth of various cancer cells in culture and implanted tumors in vivo. The biological activities of resveratrol are found to relate to its ability in modulating various targets and signaling pathway.

Piceatannol (3,5,3',4'-tetrahydroxystilbene) is a polyphenol found in grapes and other plants. It is known as a protein kinase inhibitor that exerts immunosuppressive and antitumorigenic activities on several cell lines, and has been shown to exert various pharmacological effects on immune and cancer cells (Kim et al, 2008b and references therein). In humans, piceatannol is produced as a major metabolite of resveratrol by CYP1B1 and CYP1A2 (Potter et al., 2002; Piver et al., 2004). In addition, the metabolism of trans-resveratrol into two major metabolites, piceatannol (3,5,3',4'-tetrahydroxystilbene) and another tetrahydroxystilbene, was catalyzed by recombinant human CYP1A1, CYP1A2 and CYP1B1 (Piver et al., 2004).

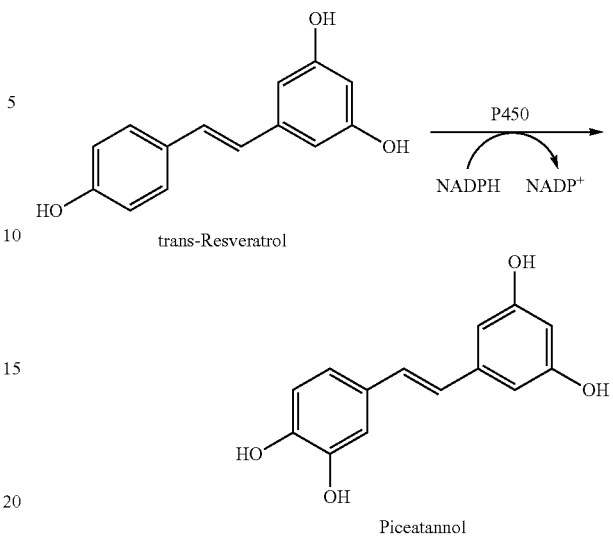

trans-Resveratrol

Piceatannol

Cytochrome P450 enzymes (P450s or CYPs) constitute a large family of enzymes that are remarkably diverse oxygenation catalysts found throughout nature, from archaea to humans (available on the internet at drnelson.utmem.edu/CytochromeP450.html). Because of their catalytic diversity and broad substrate range, P450s are attractive as biocatalysts in the production of fine chemicals, including pharmaceuticals (Guengerich 2002; Urlacher et al., 2006; Yun et al., 2007; Lamb et al., 2007). In spite of the potential use of mammalian P450s in various biotechnology fields, they are not suitable as biocatalysts because of their low stability, catalytic activity, and availability.

If a metabolite, such as piceatannol, has a biological activity, direct administration of the metabolite into a living body may be beneficial. However, large quantities of the metabolite need to be produced. If pro-drugs are converted to biologically 'active metabolites' by human liver P450s during the drug development process (Johnson et al., 2004), large quantities of the pure metabolites are required to understand the drug's efficacy, toxic effect, and pharmacokinetics.

The pure metabolites may be difficult to synthesize. An alternative to chemical synthesis is to use P450s to generate the metabolites of drugs or drug candidates. Hepatic microsomes can be a source of human P450s, but their limited availability make their use in preparative-scale metabolite synthesis impractical. Some human enzymes can also be obtained by expression of recombinant hosts. Metabolite preparation has been demonstrated using human P450s expressed in Escherichia coli and in insect cells (Parikh et al., 1997; Rushmore et al., 2000; Vail et al., 2005), but these systems are costly and have low productivities due to limited stabilities and slow reaction rates (usually <5 min$^{-1}$ (Guengerich et al., 1996)). An alternative approach to preparing the human metabolites is to use an engineered bacterial P450 that has the appropriate specificity.

The P450 BM3 (CYP102A1) from Bacillus megaterium has strong similarity to eukaryotic members of the CYP4A (fatty acid hydroxylase) family. It was shown that engineered CYP102A1 mutants could oxidize several human P450 substrates to produce the authentic metabolites with higher activities (Kim et al., 2008; Otey et al., 2005; Yun et al., 2007 and references therein). Furthermore, CYP102A1 is a versatile monooxygenase with a demonstrated ability to work on a diversity of substrates (Bernhardt et al., 2006, Di Nardo et al., 2007).

Recently, wild-type CYP102A1 has been engineered to oxidize compounds showing little or no structural similarity to its natural substrate fatty acids (Lamb et al., 2007). The compounds include testosterone, several drug-like molecules, and polycyclic aromatic hydrocarbons (PAHs), which are known substrates of human P450 enzymes (Carmichael et al., 2001; van Vugt-Lussenburg et al., 2006). However, there has been no research on whether resveratrol can be used as a substrate. A set of CYP102A1 mutants was shown to generate larger quantities of the authentic human metabolites of drugs, which may be difficult to synthesize (Otey et al., 2005). An alternative approach to preparing the metabolites is to use engineered CYP102A1 enzymes with desired properties.

Based on the scientific literature, several amino acid residues in CYP102A1 were mutated to generate mutant enzymes showing increased activity toward human P450 substrates (Yun et al., 2007). Very recently, it was reported that some selected mutations enabled the CYP102A1 enzyme to catalyze O-deethylation and 3-hydroxylation of 7-ethoxycoumarin, which are the same reactions catalyzed by human P450s (Kim et al., 2008a).

There are several patent applications related to piceatannol. That is, a composition for antihypertensive effects comprising a Rhei Rhizome extract or active compounds isolated therefrom is disclosed in Korean Patent Application No. 10-2005-0126879, and a cosmetic composition containing piceatannol and vitamin A is disclosed in Korean Patent Application No. 10-2007-0025087. However, a patent application related to a method of preparing piceatannol has not been filed. While a method of chemically synthesizing resveratrol and piceatannol is disclosed in WO2008012321, a method of biologically preparing resveratrol and piceatannol has not been disclosed.

All cited references are incorporated herein by reference in their entireties. The information disclosed herein is intended to assist the understanding of technical backgrounds of the present invention, and cannot be prior art.

DETAILED DESCRIPTION OF THE INVENTION

Technical Problem

The present invention provides a method of preparing piceatannol using an enzyme which stably and efficiently catalyzes oxidation of resveratrol into piceatannol.

Technical Solution

While searching for a method of preparing piceatannol, the present inventors found that bacterial P450 (CYP102A1) and mutants thereof may be selectively used to produce metabolites of resveratrol in humans, particularly piceatannol.

Advantageous Effects

The present invention provides a method of producing large quantities of piceatannol, which is about 60 times more expensive than resveratrol, from resveratrol, and a composition and a kit therefor.

While metabolites of resveratrol produced using the human CYP1A2 include piceatannol and other hydroxylated products, piceatannol may be selectively produced by CYP102A1 or mutants thereof.

In addition, in an in vitro system, human CYP1A2 may be inactivated by the metabolites of the human CYP1A2 itself. However, wild-type CYP102A1 or mutants of CYP102A1 may not be inactivated by the metabolites.

Even though chemical synthesis of piceatannol has been reported, biological synthesis of piceatannol using enzymes is effective and environmentally friendly in terms of white biotechnology.

BRIEF DESCRIPTION OF THE DRAWINGS

FIG. 6 illustrates the stability of P450 enzymes measured by CO-difference spectra during the oxidation of resveratrol by the P450 enzymes in the presence of NADPH. Value of 100% represents the P450 concentration before the incubation of the reaction mixture. Mutants #10, 11, 14, and 15 showed the highest stability.

FIG. 7 shows amino acid sequence of CYP102A1 (SEQ ID NO:16).

BEST MODE FOR CARRYING OUT THE INVENTION

Figure 1:
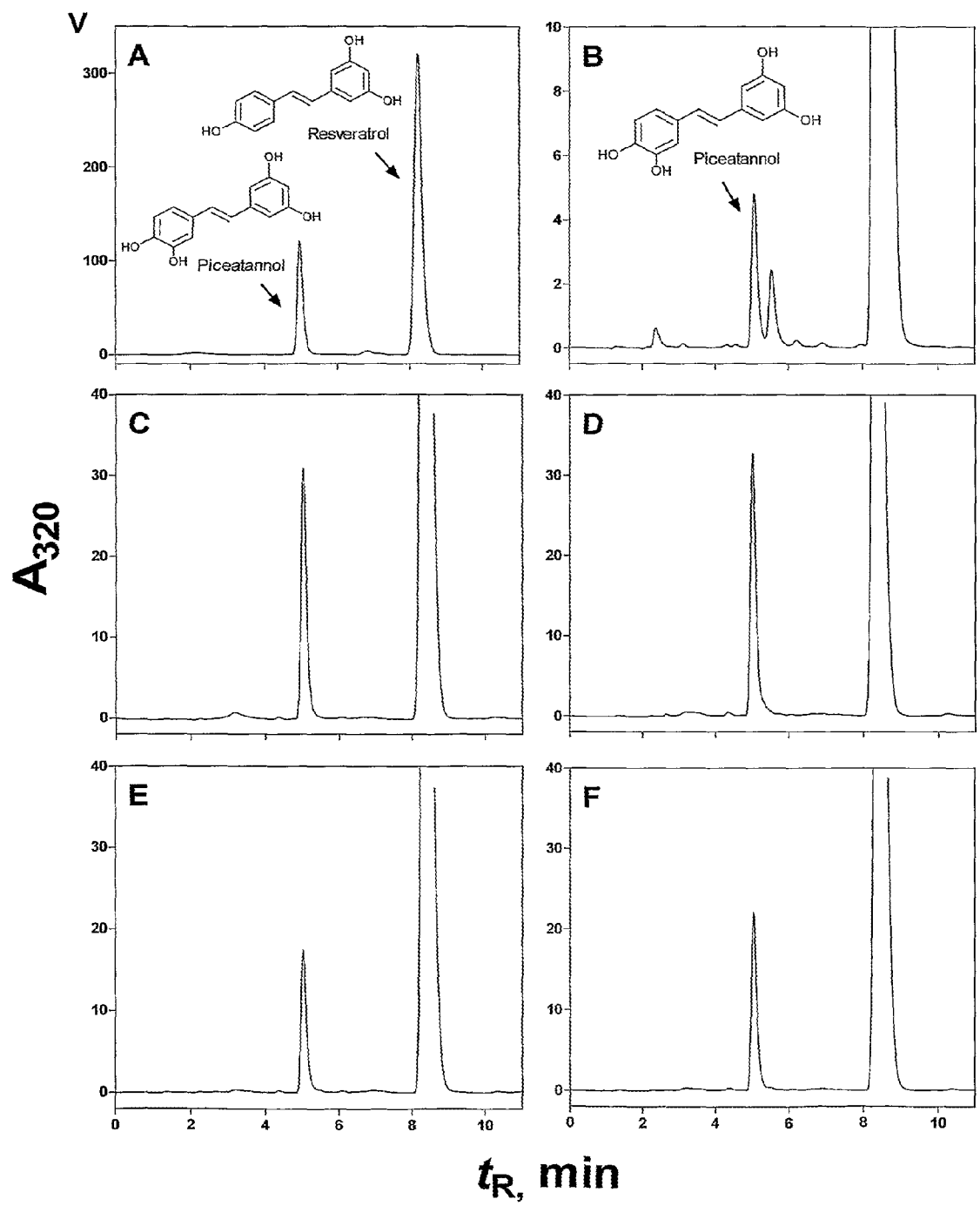
FIG. 1 illustrates HPLC chromatograms of resveratrol metabolites produced by human CYP1A2 and bacterial CYP102A1 mutants (A: resveratrol and piceatannol standards, B: human CYP1A2, C: Mutant #10, D: Mutant #13, E: Mutant #14, and F: Mutant #15). Peaks of the substrate resveratrol and two major products are indicated. UV absorbance was monitored at 320 nm.

The present invention provides a method of preparing piceatannol, and more particularly, a method of preparing piceatannol from resveratrol using bacterial cytochrome P450 BM3 (CYP102A1) or mutants thereof, and a composition and a kit therefor.

The present inventors have found that bacterial CYP102A1 and mutants thereof may act as a catalyst for oxidation of resveratrol known as a substrate of human P450. In particular, while metabolites of resveratrol produced by the human CYP1A2, as a catalyst, include piceatannol and other hydroxylated products, piceatannol may be selectively produced by CYP102A1 or mutants thereof, as a catalyst. Although human CYP1A2 is inactivated in vitro by the metabolites, wild-type CYP102A1 or mutants of CYP102A1 are not inactivated in vitro by the metabolites.

Specifically, the present inventors have identified that trans-resveratrol is converted into hydroxylated metabolites when large quantities of wild-type CYP102A1 and site-directed mutants of CYP102A1 are expressed in *E. coli* (Tables 1 and 2), and the wild-type and mutants of CYP102A1 are subjected to a reaction with trans-resveratrol and an NADPH-generating system, using HPLC (FIG. 1) and GC-MS spectra (FIGS. 2 to 5). The human CYP1A2 oxidizes resveratrol to produce two major metabolites: piceatannol and other hydroxylated products. On the other hand, wild-type CYP102A1 and mutants of CYP102A1 selectively produce only one major metabolite: piceatannol.

Turnover numbers of trans-resveratrol oxidation (piceatannol formation) by CYP102A1 mutants are measured. As a result, mutants #8 to #17 showed higher catalytic activities than that of wild-type CYP102A1. Mutant #13 has about 18-fold higher activity than the wild-type CYP102A1 (Table 3). After 1 or 2 hours of hydroxylation of resveratrol by CYP102A1 mutants, the total turnover number (TTN; mol product/mol catalyst) of the piceatannol formation is measured. As a result, mutant #13 shows the highest activity and has about 10-fold higher activity than human CYP1A1. The amount of products obtained by 1 hour-hydroxylation by human CYP1A2 is less than that obtained by 2 hour-hydroxylation by human CYP1A2. This is inferred because the human CYP1A2 is unstable or the activity of the human CYP1A2 is inhibited by the metabolites.

Kinetic parameters for 3'-hydroxylation of resveratrol by wild-type CYP102A1 and mutants of CYP102A1 are measured. Mutant #13 shows the highest $k_{cat}$ and $K_m$ and the highest catalytic efficiency ($k_{cat}/K_m$) (Table 4). In case of human CYP1A2, kinetic parameters could not be obtained. This is inferred because human P450 is inactivated by the metabolites of human P450 itself. Thus, human CYP1A2 may not be used in an in vitro system, but wild-type CYP102A1 or mutants of CYP102A1 may be used therein.

Resveratrol acts as a substrate and an inhibitor to human CYP1A2 at the same time. Piceatannol, the major metabolite of resveratrol, is also known as an inhibitor to human CYP1A2. Thus, the stability of P450 enzymes is measured during oxidation of resveratrol by P450 enzymes in the presence of NADPH using CO-difference spectra. As a result, mutants #10, 11, 14, and 15 show the highest stability (FIG. 6).

Based on these results, the present invention provides a composition for preparing piceatannol from resveratrol, the composition including wild-type CYP102A1 and/or mutants of CYP102A1.

The present invention also provides a method of preparing piceatannol, the method including reacting at least one enzyme selected from a group consisting of wild-type and mutants of CYP102A1 with resveratrol. The method may further include adding an NADPH-generating system.

The present invention also provides a kit for preparing piceatannol from resveratrol, the kit including at least one enzyme selected from a group consisting of wild-type CYP102A1 and mutants of CYP10212 and an NADPH-generating system. The kit may further include a reagent required for the progression of the reaction.

The NADPH-generating system used for the method and the kit may be any known system. For example, the NADPH-generating system may be glucose 6-phosphate dehydrogenase, NADP+, and yeast glucose 6-phosphate, but is not limited thereto.

The piceatannol formation may be performed at a temperature ranging from about 0° C. to about 40° C., preferably from about 30° C. to about 40° C.

Mutagenesis of CYP102A1 may be performed using known methods such as deletion mutagenesis (Kowalski D. et al., J. Biochem., 15, 4457), PCT method, Kunkel method, site-directed mutagenesis, DNA shuffling, StEP (staggered extension process), error-prone PCR, etc.

The mutants of CYP102A1 may have a sequence modified by natural or artificial substitution, deletion, addition, and/or insertion of amino acid of the wild-type CYP102A1. The amino acid may be substituted with an amino acid with similar properties. For example, alanine, valine, leucine, isoleucine, proline, methionine, phenylalanine, and tryptophan are non-polar amino acids with similar properties. Neutral amino acids are glycine, serine, threonine, cysteine, tyrosine, asparagine, and glutamine, acidic amino acids are aspartic acid, glutamic acid, and basic amino acids are lysine, arginine, and histidine.

The mutants of CYP102A1 include polypeptide with an amino acid sequence which is more than 50% similar, preferably more than 75% similar, and more preferably more than 90% similar to the sequence of wild-type CYP102A1.

The mutants of CYP102A1 may be prepared by at least one selected from a group consisting of: substituting $47^{th}$ amino acid arginine (R) of wild-type CYP102A1 with one amino acid selected from a group consisting of alanine, valine, leucine, isoleucine, proline, methionine, phenylalanine, and tryptophan, substituting $51^{st}$ amino acid tyrosine (Y) of wild-type CYP102A1 with one amino acid selected from a group consisting of phenylalanine, alanine, valine, leucine, isoleucine, proline, methionine, tryptophan, substituting $64^{th}$ amino acid glutamic acid (E) of wild-type CYP102A1 with one amino acid selected from a group consisting of glycine, serine, threonine, cysteine, tyrosine, asparagine, and glutamine, substituting $74^{th}$ amino acid alanine (A) of wild-type CYP102A1 with one amino acid selected from a group consisting of glycine, serine, threonine, cysteine, tyrosine, asparagine, and glutamine, substituting $81^{st}$ amino acid phenylalanine (F) of wild-type CYP102A1 with one amino acid selected from a group consisting of alanine, valine, leucine, isoleucine, proline, methionine, and tryptophan, substituting $86^{th}$ amino acid leucine (L) of wild-type CYP102A1 with one amino acid selected from a group consisting of alanine, valine, isoleucine, proline, methionine, phenylalanine, and tryptophan, substituting $87^{th}$ amino acid phenylalanine (F) of wild-type CYP102A1 with one amino acid selected from a group consisting of alanine, valine, leucine, isoleucine, proline, methionine, and tryptophan, substituting $143^{rd}$ amino acid glutamic acid (E) of wild-type CYP102A1 with one amino acid selected from a group consisting of glycine, serine, threonine, cysteine, tyrosine, asparagine, and glutamine, substituting $188^{th}$ amino acid leucine (L) of wild-type CYP102A1 with one amino acid selected from a group consisting of glycine, serine, threonine, cysteine, tyrosine, asparagine, and glutamine, and substituting $267^{th}$ amino acid glutamic acid (E) of wild-type CYP102A1 with one amino acid selected from a group consisting of alanine, valine, leucine, isoleucine, proline, methionine, phenylalanine, and tryptophan.

Preferably, the mutants of CYP102A1 may be prepared by at least one selected from a group consisting of: substituting $47^{th}$ amino acid arginine (R) of wild-type CYP102A1 with leucine (L), substituting $51^{st}$ amino acid tyrosine (Y) of wild-type CYP102A1 with phenylalanine, substituting $64^{th}$ amino acid glutamic acid (E) of wild-type CYP102A1 with glycine (G), substituting $74^{th}$ amino acid alanine (A) of wild-type CYP102A1 with glycine (G), substituting $81^{st}$ amino acid phenylalanine (F) of wild-type CYP102A1 with isoleucine (I), substituting $86^{th}$ amino acid leucine (L) of wild-type CYP102A1 with isoleucine (I), substituting 87$^{th}$ amino acid phenylalanine (F) of wild-type CYP102A1 with valine (V), substituting 143$^{rd}$ amino acid glutamic acid (E) of wild-type CYP102A1 with glycine (G), substituting 188$^{th}$ amino acid leucine (L) of wild-type CYP102A1 with glutamine (Q), and substituting 267$^{th}$ amino acid glutamic acid (E) of wild-type CYP102A1 with valine (V).

More preferably, the mutants of CYP102A1 may include amino acid substitution sites of wild-type CYP102A1 selected from a group consisting of F87A, R47L/Y51F, A74G/F87V/L188Q, R47L/L86I/L188Q, R47L/F87V/L188Q, R47L/F87V/L188Q/E267V, R47L/L86I/L188Q/E267V, R47L/L86I/F87V/L188Q, R47L/F87V/E143G/L188Q/E267V, R47L/E64G/F87V/E143G/L188Q/E267V, R47L/F81I/F87V/E143G/L188Q/E267V, and R47L/E64G/F81I/F87V/E143G/L188Q/E267V.

Protein according to the present invention may be prepared using methods known in the art, for example, genetic engineering techniques, solid-phase peptide synthesis (Merrifield, J. Am. Chem. Soc., 85:2149-2154 (1963)), or method of cleaving protein using peptidases. Protein according to the present invention may be natural protein, or may be prepared by a recombination of culturing cells transformed with DNA encoding CYP102A1 or mutants thereof and collecting the protein. Protein may be prepared by inserting nucleic acid molecules encoding protein according to the present invention into an expression vector, transforming the vector into a host cell, and purifying protein expressed by the transformed host cell.

The vector may be plasmid, cosmid, a virus, or phage. The host cell into which DNA in the vector is cloned or expressed may be a prokaryotic cell, a yeast cell, and a eukaryotic cell. Culture conditions such as a culture medium, temperature, and pH may be selected by those of ordinary skill in the art without undue experiment. In general, principles, protocols, and techniques to maximize productivity of the culture of cells are disclosed in Mammalian Cell Biotechnology: a Practical Approach, M. Butler, ed. (IRL Press, 1991).

The expression and cloning vector may include a promoter operationally linked to a nucleic acid sequence that encodes CYP102A2 or mutants thereof which induce the synthesis of mRNA. Various promoters recognized by host cells are known. A promoter suitable for a prokaryotic host cell may be β-lactamase and a lactose promoter system, alkali phosphatase, a tryptophan (trp) promoter system, and a hybrid promoter, for example a tac promoter. In addition, the promoter used in bacterial systems may include a Shine-Dalgarno (SD) sequence operationally linked to DNA that encodes protein. A promoter suitable for a yeast host cell may include 3-phosphoglycerate kinase or other glucosidases.

The present invention will now be described in greater detail with reference to the following examples, which are for illustrative purposes only and are not intended to limit the scope of the invention.

EXAMPLES

Trans-resveratrol, trans-piceatannol, and NADPH were purchased from Sigma-Aldrich (Milwaukee, Wis., USA). Other chemicals were of the highest grade commercially available. Human CYP1A2 was prepared as disclosed by Kim et al., (2008c).

Example 1

Construction of P450 BM3 Mutants by Site-Directed Mutagenesis

Site-directed mutants of CYP102A1 were prepared as disclosed by Kim et al., *Drug Metab Dispos*, volume 35, p. 2166-2170, 2008. PCR primers used to introduce BamHI/SacI restriction sites and to induce mutation are listed in Table 1. Codons for amino acid substitution are in italics and underlined. The PCR primers were obtained from Genotech (Daejeon, Korea). Genes that encode CYP102A1 mutants were amplified from pCWBM3 by PCR using primers designed to facilitate cloning into an expression vector pCWori (Dr. F. W. Dahlquist, University of California, Santa Barbara, Calif.) or pSE420 (Invitrogen) (Farinas et al., 2001). Oligonucleotide assembly was performed by PCR using the 14 sets of designed primers listed in Table 1. The amplified genes were subsequently cloned into the PCWBM3 BamHI/SacI vector at the BamHI/SacI restriction sites. These plasmids were transformed into *Escherichia coli* DH5α F'IQ (Invitrogen), and this strain was also used to express the mutant CYP102A1 proteins. After mutagenesis, the presence of the desired mutations was confirmed by DNA sequencing in Genotech (Daejeon, Korea).

TABLE 1

Primers used for the generation of mutants in this study

| Name | Sequence |
|---|---|
| BamHI forward | 5'-AGC *GGA TC*C ATG ACA ATT AAA GAA ATG CCT C-3' |
| SacI reverse | 5'-ATC GAG CTC GTA GTT TGT AT-3' |
| R47L | 5'-GCG CCT GGT *CTG* GTA ACG CG-3' |
| Y51F | 5'-GTA ACG CGC *TTC* TTA TCA AGT-3' |
| E64G | 5'-GCA TGC GAT *GGC* TCA CGC TTT-3' |
| A74G | 5'-TAAGT CAA *GGC* CTT AAA TTT GTA CG-3' |
| F81I | 5'-GTA CGT GAT *ATT* GCA GGA GAC-3' |
| L86I | 5'-GGA GAC GGG *ATT* TTT ACA AGC T-3' |
| F87A | 5'-GAC GGG TTA *GCG* ACA AGC TGG-3' |
| F87V | 5'-GAC GGG TTA *GTG* ACA AGC TGG-3' |
| E143G | 5'-GAA GTA CCG *GGC* GAC ATG ACA-3' |
| L188Q | 5'-ATG AAC AAG *CAG* CAG CGA GCA A-3' |
| A264G | 5'-TTC TTA ATT *GGG* GGA CAC GTG-3' |
| E267V | 5'-T GCG GGA CAC *GTG* ACA ACA AGT-3' |
| L86I/F87V | 5'-GGA GAC GGG *ATT GTG* ACA AGC TG-3' |

Example 2

Expression and Purification of Wild-Type CYP102A1 and Mutants of CYP102A1

Plasmids comprising a gene of wild-type CYP102A1 and mutants of CYP102A1 (pCWBM3) were transformed into *Escherichia coli* DH5α F'-IQ. A single colony was inoculated into 5 ml of a Luria-Bertani medium supplemented with ampicillin (100 g/ml) and cultured at 37° C. This culture was inoculated into 250 ml of a Terrific Broth medium supplemented with ampicillin (100 g/ml). The cells were grown at 37° C. while shaking at 250 rpm to an OD$_{600}$ of up to 0.8, at which gene expression was induced by the addition of isopropyl-δ-D-thiogalactopyranoside to a final concentration of 0.5 mM. δ-Aminolevulinic acid (1.0 mM) was also added thereto. Following induction, the cultures were allowed to grow another 36 hours at 30° C. Cells were harvested by centrifugation (15 min, 5000 g, 4° C.). The cell pellet was resuspended in a TES buffer (100 mM Tris-HCl, pH 7.6, 500 mM sucrose, 0.5 mM EDTA) and lysed by sonication (Sonicator; Misonix, Inc., Farmingdale, N.Y.). After the lysate was centrifuged at 100,000 g (90 min, 4° C.), a soluble cytosolic fraction was collected and used for the activity assay. The soluble cytosolic fraction was dialyzed against a 50 mM potassium phosphate buffer (pH 7.4) and stored at −80° C. Enzymes were used within 1 month of manufacture.

CYP102A1 concentrations were determined from the CO-difference spectra as described by Omura and Sato (1964) using $\epsilon$=91 mM/cm. For all of the wild-type enzymes and mutated enzymes, a typical culture yielding of 300 to 700 nM P450 enzymes could be detected. The expression level of wild-type CYP102A1 and mutants of CYP102A1 was in the range of 1.0 to 2.0 nmol P450/mg cytosolic protein.

Several mutants with high catalytic activity for humans were selected, and the substitution sites in the mutants are shown in Table 2 below.

TABLE 2

CYP102A1 mutants used in this study

| Abbreviations | BM3 wild type and mutants | Ref. |
|---|---|---|
| WT | BM3 wild type | |
| Mutant #1 | F87A | Carmichael et al., 2001 |
| Mutant #2 | A264G | Carmichael et al., 2001 |
| Mutant #3 | F87A/A264G | Carmichael et al., 2001 |
| Mutant #4 | R47L/Y51F | Carmichael et al., 2001 |
| Mutant #5 | R47L/Y51F/A264G | Carmichael et al., 2001 |
| Mutant #6 | R47L/Y51F/F87A | Carmichael et al., 2001 |
| Mutant #7 | R47L/Y51F/F87A/A264G | Carmichael et al., 2001 |
| Mutant #8 | A74G/F87V/L188Q | Li et al., 2001 |
| Mutant #9 | R47L/L86I/L188Q | Kim et al., 2008a |
| Mutant #10 | R47L/F87V/L188Q | van Vugt-Lussenburg et al., 2007 |
| Mutant #11 | R47L/F87V/L188Q/E267V | van Vugt-Lussenburg et al., 2007 |
| Mutant #12 | R47L/L86I/L188Q/E267V | Kim et al., 2008 |
| Mutant #13 | R47L/L86I/F87V/L188Q | van Vugt-Lussenburg et al., 2007 |
| Mutant #14 | R47L/F87V/E143G/L188Q/E267V | Kim et al., 2008a |
| Mutant #15 | RA7L/E64G/F87V/E143G/L188Q/E267V | Kim et al., 2008a |
| Mutant #16 | R47L/F81I/F87V/E143G/L188Q/E267V | Kim et al., 2008a |
| Mutant #17 | R47L/E64G/F81I/F87V/E143G/L188Q/E267V | van Vugt-Lussenburg et al., 2007 |

Example 3

Hydroxylation of Trans-Resveratrol by Wild-Type P450 BM3 and Mutants of P450 BM3

Oxidation of trans-resveratrol, a substrate of human CYP1A2, by CYP102A1 was identified. Typical steady-state reactions for trans-resveratrol hydroxylation included 50 pmol P450 BM3 in 0.25 ml of a 100 mM potassium phosphate buffer (pH 7.4) were performed along with a specified amount of a substrate. To determine the kinetic parameter of several CYP102A1 mutants, 2 to 100 μM of trans-resveratrol was used. An NADPH-generating system was used to initiate reaction solutions (final concentrations: 10 mM glucose 6-phosphate, 0.5 mM NADP+, and 1 IU yeast glucose 6-phosphate per ml). Trans-resveratrol stocks (20 mM) were prepared in DMSO and diluted into the enzyme reactions with the final organic solvent concentration <1% (v/v). Reactions were generally incubated for 10 min at 37° C., and terminated with 105 μl of ice-cold acetic acid/methanol (95/5, v/v).

Example 3-1

HPLC Analysis

After centrifugation of the reaction mixture, the supernatant was analyzed by HPLC (Piver et al. 2004). Samples (30 μl) were injected into a Gemini $C_{18}$ column (4.6 mm×150 mm, 5 μm, Phenomenex, Torrance, Calif.). The mobile phase A was water containing 87 mM of 0.5% acetic acid/acetonitrile (95/5, v/v); whereas the mobile phase B was acetonitrile/ 0.5% acetic acid (95/5, v/v). The mobile phase A/B (75/25, v/v) was delivered at a flow rate of 1 ml·min$^{-1}$ by a gradient pump (LC-20AD, Shimadzu, Kyoto, Japan). Eluates were detected by UV rays at 320 nm.

FIG. 1 illustrates HPLC chromatograms of resveratrol metabolites produced by human CYP1A2 and bacterial CYP102A1 mutants (A: resveratrol and piceatannol standards, B: human CYP1A2, C: Mutant #10, D: Mutant #13, E: Mutant #14, and F: Mutant #15). Peaks of the substrate resveratrol and two major products are indicated. UV absorbance was monitored at 320 nm.

While human CYP1A2 oxidized resveratrol to produce two major metabolites: piceatannol and other hydroxylated products (B), wild-type CYP102A1 and mutants of CYP102A1 produced only one major metabolite. The retention time of the peak was exactly matched to that of the piceatannol standard. That is, the wild-type CYP102A1 and mutants of CYP102A1 selectively produced piceatannol when oxidizing resveratrol. Since there is no need to separate the hydroxylated product from piceatannol, the use of wild-type CYP102A1 and mutants of CYP102A1 is beneficial.

Example 3-2

GC-MS Analysis

For the identification of resveratrol metabolite, produced by P450 BM3 mutants, GC-MS analysis was done by comparing GC-profiles and fragmentation patterns of piceatannol and resveratrol. An oxidation reaction of trans-resveratrol by P450 BM3 mutants was done. The aqueous samples were extracted with ethyl acetate. After centrifugation, the organic phase was dried under nitrogen as well as the standard trans-resveratrol and piceatannol solutions (10 mM in DMSO). Then, trimethylsilyl (TMS) derivatives were prepared as follows. 100 μl of a solution of BSTFA/TMCS (99/1, v/v) (Supelco) was added to the dry residue or standard trans-resveratrol and piceatannol, and then the mixture was left for 60 min at 60° C.

GC-MS analysis was performed on a GC-2010 gas chromatograph (Shimadzu, Kyoto, Japan) with an Rtx-5 (5% diphenyl/95% dimethyl polysiloxane capillary column) (30 m×0.32 mm i.d.×0.25 μm film thickness). The injector temperature was 250° C. The derivatives of resveratrol and piceatannol were separated by GC analysis under the conditions: GC oven conditions of 60° C. for 5 min, followed by an increase of 50° C.·min$^{-1}$ up to 200° C. and then 2° C.·min$^{-1}$ up to 300° C. The gas chromatography was combined with a GCMS-QP2010 Shimazu mass spectrometer operating in an electron ionization mode (70 eV) (Piver et al. 2004).

Figure 2:
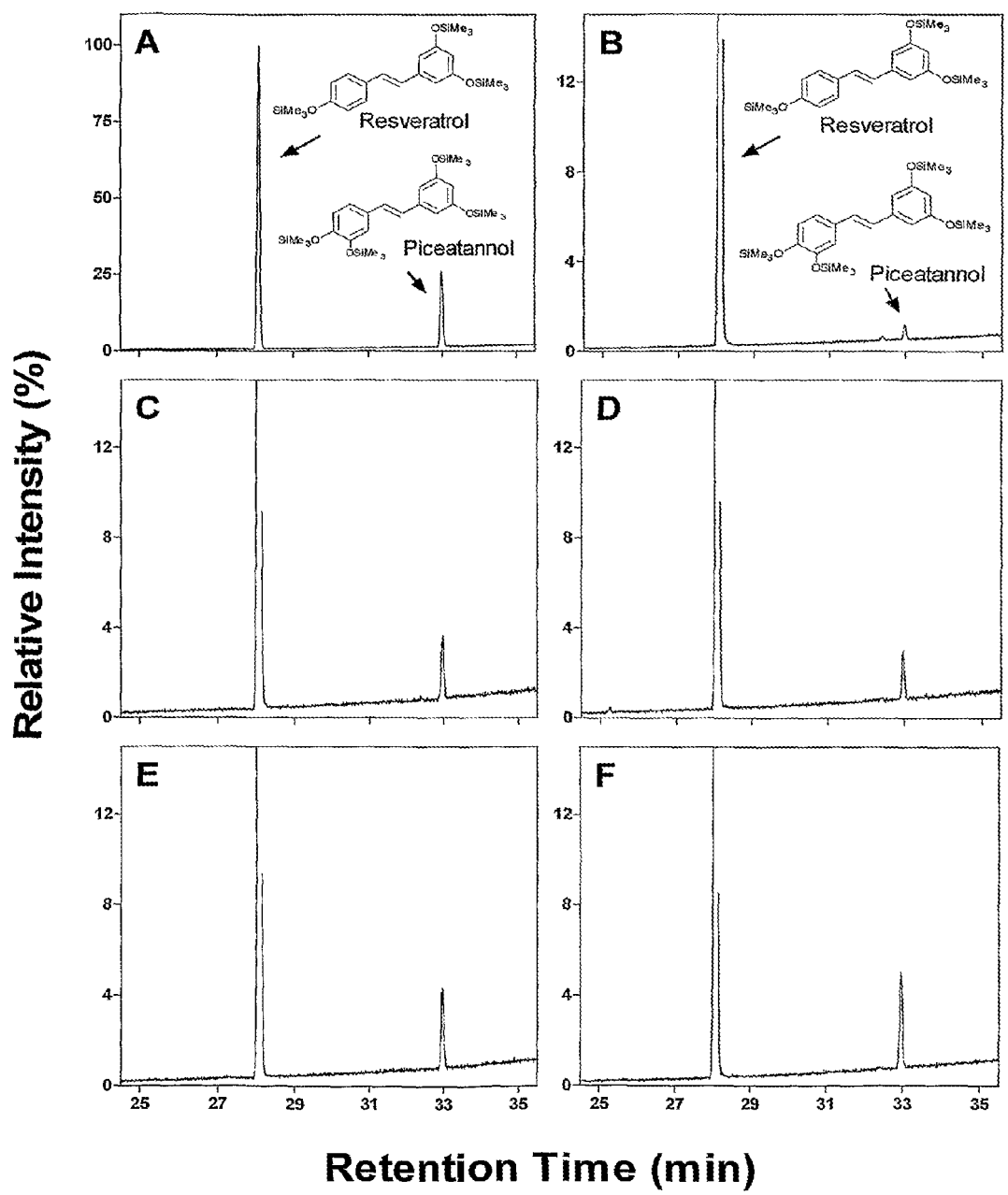
FIG. 2 illustrates GC analysis results of resveratrol metabolite derivatives produced by CYP102A1 and mutants thereof (A: trans-resveratrol and piceatannol standards, B: human CYP1A2, C: Mutant #10, D: Mutant #13, E: Mutant #14, and F: Mutant #15). The mass spectra of the reaction samples showed peaks at 28.09 min (resveratrol) and 32.98 min (piceatannol).

FIG. 2 illustrates GC analysis results of resveratrol metabolite derivatives produced by CYP102A1 and mutants thereof (A: standard trans-resveratrol and piceatannol, B: human CYP1A2, C: Mutant #10, D: Mutant #13, E: Mutant #14, and F: Mutant #15). The mass spectra of the reaction samples showed peaks at 28.09 min (resveratrol) and 32.98 min (piceatannol).

As a result of the GC-MS analysis, it was identified that the retention time and fragmentation patterns of the metabolite produced by the CYP102A1 mutants were exactly matched to those of the piceatannol standard, and thus the metabolite produced by the CYP102A1 mutants was piceatannol. Although piceatannol and other hydroxylated products were found as the two major metabolites of resveratrol by human liver microsomes, all wild-type CYP102A1 and mutants of CYP102A1 showed only one hydroxylated product, i.e., piceatannol. The human P450 1A2, the major enzyme for hydroxylation reactions of resveratrol in human liver, also showed a preference for the 3'-hydroxylation reaction over the hydroxylation reaction at other position humans (B of FIG. 2 and FIG. 4). However, unlike the human P450 enzyme, wild-type CYP102A1 and mutants of CYP102A1 produced only piceatannol without producing other hydroxylated products.

Figure 3:
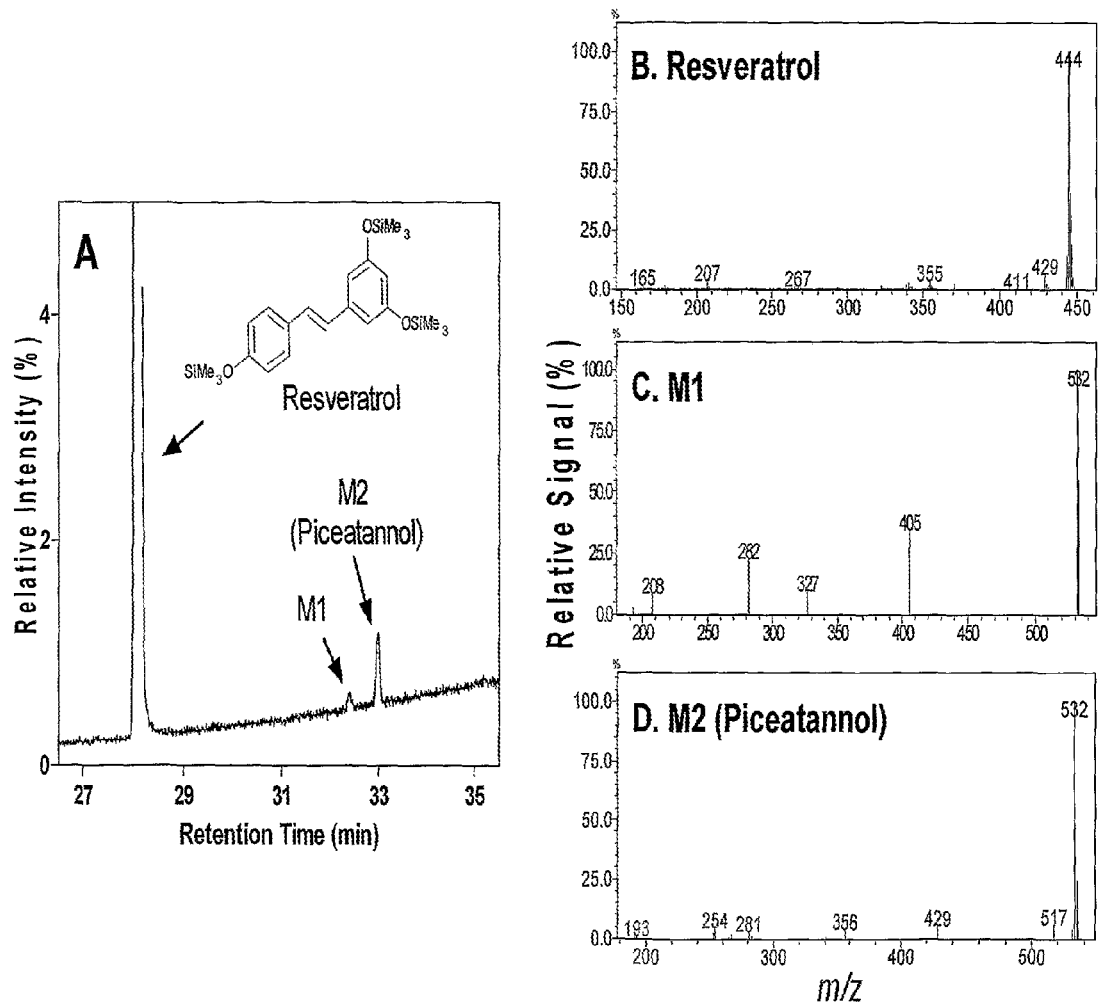
FIG. 3 illustrates GC elution profiles (A) and MS spectra (B: resveratrol, C and D: resveratrol metabolites) of resveratrol metabolite derivatives produced by human CYP1A2.

FIG. 3 illustrates GC elution profiles (A) and MS spectra (B: resveratrol, C and D: resveratrol metabolites) of trans-resveratrol metabolite derivatives produced by human CYP1A2.

Figure 4:
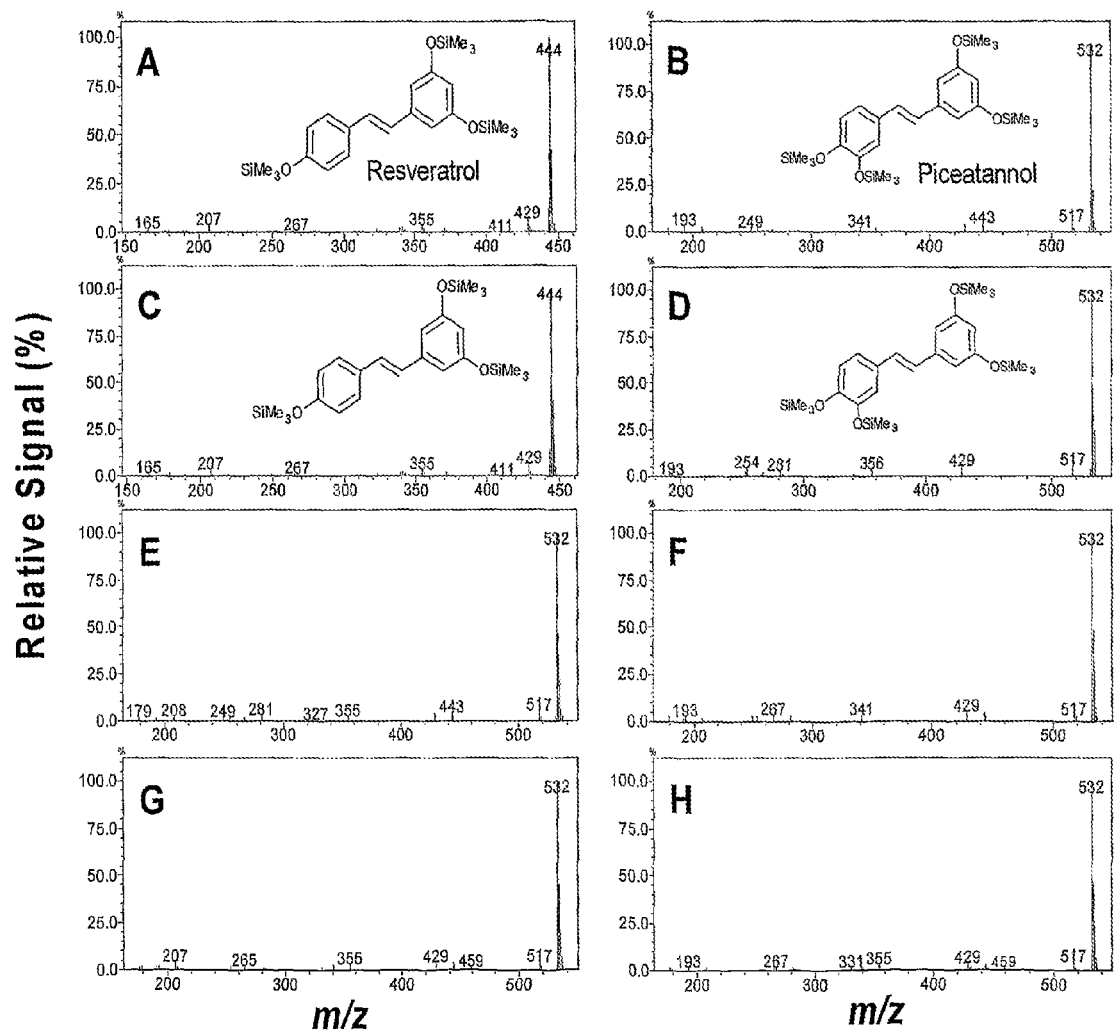
FIG. 4 illustrates MS spectra of peaks of metabolites produced by standard trans-resveratrol (A) and piceatannol (B) that were eluted at 29.08 min and 32.98 min (Res-TMS; m/z=444, Pic-TMS; m/z=532), peaks of metabolites produced by human CYP1A2 that were eluted at 29.08 min and 32.98 min (C: Res-TMS; m/z=444, D: Pic-TMS; m/z=532), and peaks of metabolites produced by CYP102A1 mutants that were eluted at 32.98 min (Pic-TMS; m/z=532) (E: Mutant #10, F: Mutant #13, G: Mutant #14, and H: Mutant #15).

FIG. 4 illustrates MS spectra of peaks of metabolites produced by standard trans-resveratrol (A) and piceatannol (B) that were eluted at 29.08 min and 32.98 min (Res-TMS; m/z=444, Pic-TMS; m/z=532), peaks of metabolites produced by human CYP1A2 that were eluted at 29.08 min and 32.98 min (C: Res-TMS; m/z=444, D: Pic-TMS; m/z=532), and peaks of metabolites produced by CYP102A1 mutants that were eluted at 32.98 min (Pic-TMS; m/z=532) (E: Mutant #10, F: Mutant #13, G: Mutant #14, and H: Mutant #15).

Example 3-3

Determination of Total Turnover Number

To determine the total turnover number of CYP102A1 mutants, 100 μM of trans-resveratrol was used. The reaction was initiated by the addition of the NADPH-generating system, incubated for 1 and 2 hours, respectively, at 30° C. The formation rate of piceatannol was determined by HPLC as described above.

Table 3 shows turnover numbers of 17 mutants for trans-resveratrol oxidation (piceatannol formation). The ability of wild-type P450 BM3 and mutants of P450 BM3 to oxidize trans-resveratrol was measured at a fixed substance concentration (100 μM).

TABLE 3

Rates of piceatannol formation by various CYP102A1 mutants[a]

| Enzyme | nmol product/min/nmol P450 Piceatannol |
|---|---|
| WT | 0.22 ± 0.01 |
| Mutant | |
| #1 | 0.021 ± 0.001 |
| #2 | ND[b] |
| #3 | ND[b] |
| #4 | 0.027 ± 0.001 |

TABLE 3-continued

Rates of piceatannol formation by various CYP102A1 mutants[a]

| Enzyme | nmol product/min/nmol P450 Piceatannol |
|---|---|
| #5 | ND[b] |
| #6 | ND[b] |
| #7 | ND[b] |
| #8 | 1.1 ± 0.1 |
| #9 | 0.24 ± 0.01 |
| #10 | 1.6 ± 0.1 |
| #11 | 0.64 ± 0.03 |
| #12 | 0.33 ± 0.03 |
| #13 | 4.0 ± 0.1 |
| #14 | 1.3 ± 0.1 |
| #15 | 1.9 ± 0.3 |
| #16 | 0.97 ± 0.1 |
| #17 | 1.8 ± 0.1 |

Mutants #8 to #17 showed higher catalytic activities than that of wild-type CYP102A1. Mutant #13 showed about 18-fold higher activity than the wild-type CYP102A1.

Figure 5:
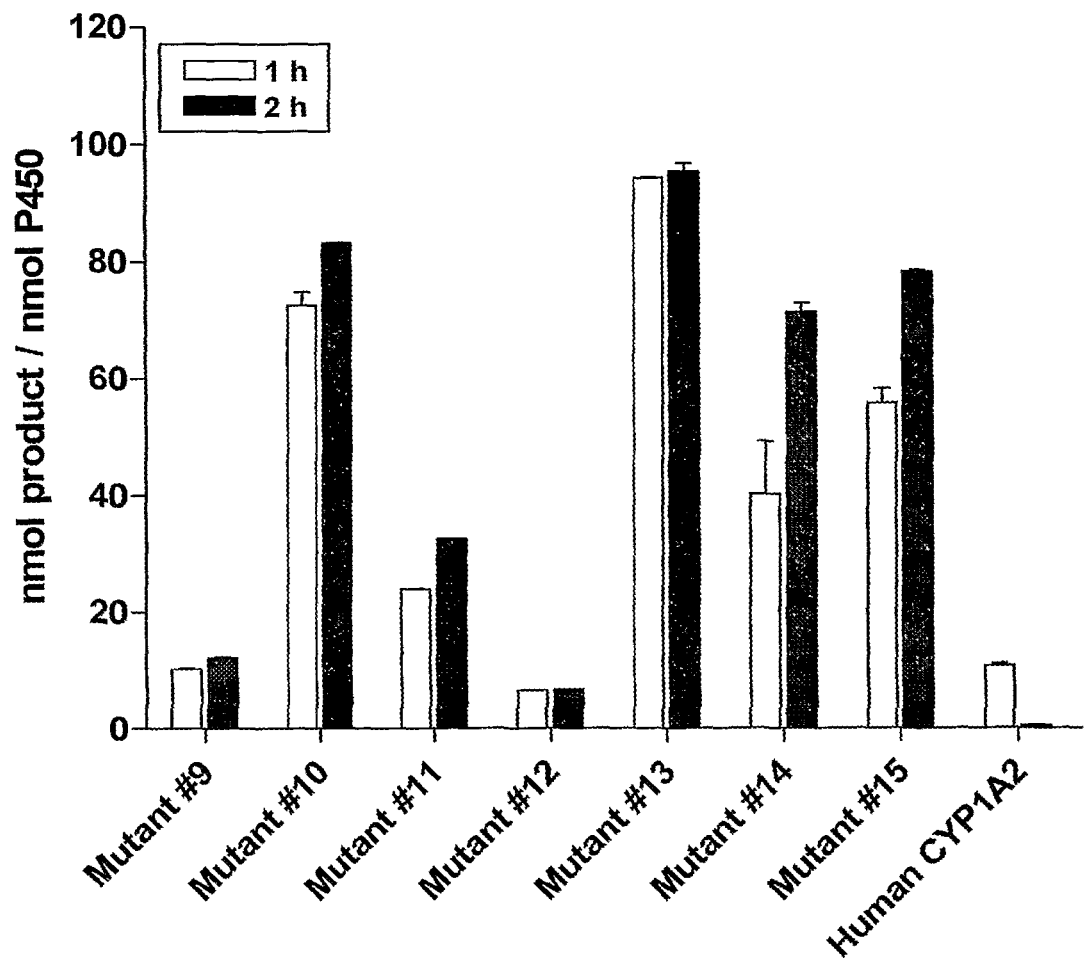
FIG. 5 illustrates total turnover numbers (TTN; mol product/mol catalyst) of piceatannol formation by CYP102A1 mutants. 100 µM trans-resveratrol was used. The reaction was initiated by the addition of the NADPH-generating system, incubated for 1 or 2 hours, respectively, at 30° C. The formation rate of piceatannol was determined by HPLC.

FIG. 5 illustrates total turnover numbers (TTN; mol product/mol catalyst) piceatannol formation by CYP102A1 mutants. 100 μM trans-resveratrol was used. The reaction was initiated by the addition of the NADPH-generating system, incubated for 1 or 2 hours, respectively, at 30° C. The formation rate of piceatannol was determined by HPLC as described above.

Mutant #13 showed the highest activity and has about 10-fold higher activity than human CYP1A1. Meanwhile, the amount of products obtained by 1 hour-hydroxylation by human CYP1A2 is less than that obtained by 2 hour-hydroxylation by human CYP1A2. This was inferred because CYP1A2 is unstable or the activity of the human CYP1A2 is inhibited by the metabolites.

Example 3-4

Determination of Kinetic Parameters

Kinetic parameters ($K_m$ and $k_{cat}$) were determined using nonlinear regression analysis with GraphPad PRISM software (GraphPad, San Diego, Calif., USA). The data were analyzed using the standard Michaelis-Menten equation: $v=k_{cat}[E][S]/([S]+K_m)$, where the velocity of the reaction is a function of the rate-limiting step in turnover ($k_{cat}$), the enzyme concentration ([E]), substrate concentration ([S]), and the Michaelis constant ($K_m$).

Table 4 shows kinetic parameters for 3'-hydroxylation of resveratrol by wild-type CYP102A1 and mutants of CYP102A1.

TABLE 4

Kinetic parameters of piceatannol formation by CYP102A1 mutants

| P450 BM3 | Piceatannol formation | | |
|---|---|---|---|
| | $k_{cat}(min^{-1})$ | $K_m(μM)$ | $k_{cat}/K_m$ |
| Mutant #9 | 0.20 ± 0.02 | 66 ± 14 | 0.0030 ± 0.0007 |
| Mutant #10 | 1.1 ± 0.1 | 30 ± 13 | 0.037 ± 0.016 |
| Mutant #11 | 0.12 ± 0.01 | 2.7 ± 0.7 | 0.044 ± 0.012 |
| Mutant #12 | 0.13 ± 0.01 | 54 ± 11 | 0.0024 ± 0.0005 |
| Mutant #13 | 6.7 ± 0.3 | 15 ± 3 | 0.45 ± 0.09 |
| Mutant #14 | 0.58 ± 0.04 | 13 ± 3 | 0.046 ± 0.011 |
| Mutant #15 | 0.54 ± 0.02 | 16 ± 2 | 0.038 ± 0.005 |

Mutant #13 showed the highest $k_{cat}$ and $K_m$ and the highest catalytic efficiency ($k_{cat}/K_m$).

In case of human CYP1A2, kinetic parameters could not be obtained. This is inferred because P450 is inactivated by the metabolites of P450 itself (Chun et al., 1999, 2001). Thus, human CYP1A2 may not be used in an in vitro system, but wild-type CYP102A1 or mutants of CYP102A1 may be used therein.

Example 4

Stability of CYP102A1 Mutants

It is known that metabolites of resveratrol are potent inhibitors against human CYPs, i.e., CYP1A1, 1A2, and 1B1 (Chun et al., 1999, 2001). Resveratrol acts as a substrate and inhibitor to human CYP1A2 at the same time (Fairman et al., 2007; Piver et al., 2004). Piceatannol, the major metabolite of resveratrol, is also known as a potent inhibitor to human CYP1A2 (Mikstacka et al., 2006).

FIG. 6 illustrates the stability of P450 enzymes measured by CO-difference spectra during the oxidation of resveratrol by the P450 enzymes in the presence of NADPH. Value of 100% represents the P450 concentration before the incubation of the reaction mixture. Mutants #10, 11, 14, and 15 showed the highest stability.

While the present invention has been particularly shown and described with reference to exemplary embodiments thereof, it will be understood by those of ordinary skill in the art that various changes in form and details may be made therein without departing from the spirit and scope of the present invention as defined by the following claims.

REFERENCES

Athar M, Back J H, Tang X, Kim K H, Kopelovich L, Bickers D R, Kim A L (2007) Resveratrol: a review of preclinical studies for human cancer prevention. *Toxicol Appl Pharmaco.* 224:274-283.

Bernhardt R (2006) Cytochromes P450 as versatile biocatalysts. *J Biotechnol* 124:128-145.

Carmichael A B and Wong L L (2001) Protein engineering of *Bacillus megaterium* CYP102. The oxidation of polycyclic aromatic hydrocarbons. *Eur J Biochem* 268:3117-3125.

Chun Y J, Kim S, Kim D, Lee S K, Guengerich F P. (2001) A new selective and potent inhibitor of human cytochrome P450 1B1 and its application to antimutagenesis. *Cancer Res* 61:8164-8170.

Chun Y J, Kim M Y, Guengerich F P. (1999) Resveratrol is a selective human cytochrome P450 1 A1 inhibitor. *Biochem Biophys Res Commun* 262:20-24.

Di Nardo G, Fantuzzi A, Sideri A, Panicco P, Sassone C, Giunta C and Gilardi G (2007) Wild-type CYP102A1 as a biocatalyst: turnover of drugs usually metabolised by human liver enzymes. *J Biol Inorg Chem* 12:313-323.

Farinas E T, Schwaneberg U, Glieder A and Arnold F H (2001) Directed evolution of a cytochrome P450 monooxygenase for alkane oxidation. *Advanced Synthesis & Catalysis* 343:601-606.

Fairman D A, Collins C, Chapple S (2007) Progress curve analysis of CYP1A2 inhibition: a more informative approach to the assessment of mechanism-based inactivation *Drug Metab Dispos* 35:2159-2165.

Guengerich F P (2002) Cytochrome P450 enzymes in the generation of commercial products. *Nat Rev Drug Discov* 1:359-366.

Guengerich F P, Gillam E M, Shimada T (1996) New applications of bacterial systems to problems in toxicology. *Crit Rev Toxicol* 26: 551-583.

Johnson M D, Zuo H, Lee K, Trebley J P, Rae J M, Weatherman R V, Zeruesanay D, Flockhart D A, Skaar T C (2004) Pharmacological characterization of 4-hydroxy-N-desmethyl tamoxifen, a novel metabolite of tamoxifen. *Breast Cancer Res Treat* 207:1-9.

Kim D H, Kim K H, Kim D H, Liu K H, Jung H C, Pan J G, Yun C H (2008a) Generation of human metabolites of 7-ethoxycoumarin by bacterial cytochrome P450 BM3. *Drug Metab Dispos* 36:2166-2170.

Kim Y H, Kwon H S, Kim D H, Cho H J, Lee H S, Jun J G, Park J H, Kim J K (2008b) Piceatannol, a stilbene present in grapes, attenuates dextran sulfate sodium-induced colitis. *Int Immunopharmacol* 8:1695-1702.

Kim D H, Kim K H, Isin E M, Guengerich F P, Chae H Z, Ahn T, Yun C H. (2008c) Heterologous expression and characterization of wild-type human cytochrome P450 1A2 without conventional N-terminal modification in *Escherichia coli. Protein Expr Purif.* 57:188-200.

Kundu J K, Surh Y J (2008) Cancer chemopreventive and therapeutic potential of resveratrol: mechanistic perspectives. *Cancer Lett* 269:243-261.

Lamb D C, Waterman M R, Kelly S L and Guengerich F P (2007) Cytochromes P450 and drug discovery. *Curr Opin Biotechnol* 18:504-512.

Li Q S, Ogawa J, Schmid R D and Shimizu S (2001) Engineering cytochrome P450 BM-3 for oxidation of polycyclic aromatic hydrocarbons. *Appl Environ Microbiol* 67:5735-5739.

Mikstacka R, Rimando A M, Szalaty K, Stasik K, Baer-Dubowska W (2006) Effect of natural analogues of trans-resveratrol on cytochromes P4501A2 and 2E1 catalytic activities. *Xenobiotica* 36:269-285.

Narhi L O and Fulco A J (1982) Phenobarbital induction of a soluble cytochrome P-450-dependent fatty acid monooxygenase in *Bacillus megaterium. J. Biol. Chem.* 257:2147-150.

Omura T and Sato R (1964) The carbon monoxide-binding pigment of liver microsomes. II. Solubilization, purification, and properties. *J Biol Chem* 239:2379-2385.

Otey C R, Bandara G, Lalonde J, Takahashi K and Arnold F H (2005) Preparation of human metabolites of propranolol using laboratory-evolved bacterial cytochrome P450. *Biotechnol Bioeng* 93:494-499.

Parikh A, Gillam E M, Guengerich F P (1997) Drug metabolism by *Escherichia coli* expressing human cytochromes P450. *Nat Biotechnol* 15:784-788.

Pirola L, Frojdo (2008) Resveratrol: one molecule, many targets. *IUBMB Life* 60:323-332.

Potter G A, Patterson L H, Wanogho E, Perry P J, Butler P C, Ijaz T, Ruparelia K C, Lamb J H, Farmer P B, Stanley L A, Burke M D (2002) The cancer preventative agent resveratrol is converted to the anticancer agent piceatannol by the cytochrome P450 enzyme CYP1B1. *Br J Cancer* 86:774-778.

Piver B, Fer M, Vitrac X, Merillon J M, Dreano Y, Berthou F, Lucas D. (2004) Involvement of cytochrome P450 1A2 in the biotransformation of trans-resveratrol in human liver microsomes. *Biochem Pharmacol* 68:773-782.

Rushmore T H, Reider P J, Slaughter D, Assang C, Shou M (2000) Bioreactor systems in drug metabolism: Synthesis of cytochrome P450-generated metabolites. *Metab Eng* 2:115-125.

Stottmeister U, Aurich A, Wilde H, Andersch J, Schmidt S, Sicker D (2005) White biotechnology for green chemistry: fermentative 2-oxocarboxylic acids as novel building blocks for subsequent chemical syntheses. *J Ind Microbiol Biotechnol* 32:651-664.

Urlacher V B and Eiben S (2006) Cytochrome P450 monooxygenases: perspectives for synthetic application. *Trends Biotechnol* 24:324-330.

Vail R B, Homann M J, Hanna I, Zaks A (2005) Preparative synthesis of drug metabolites using human cytochrome P450s 3A4, 2C9 and 1A2 with NADPH-P450 reductase expressed in *Escherichia coli*. *J Ind Microbiol Biotechnol* 32:67-74.

van Vugt-Lussenburg B M, Damsten M C, Maasdijk D M, Vermeulen N P and Commandeur J N (2006) Heterotropic and homotropic cooperativity by a drug-metabolizing mutant of cytochrome P450 BM3. *Biochem Biophys Res Commun* 346:810-818.

van Vugt-Lussenburg B M, Stjernschantz E, Lastdrager J, Oostenbrink C, Vermeulen N P and Commandeur J N (2007) Identification of critical residues in novel drug-metabolizing mutants of cytochrome P450 BM3 using random mutagenesis. *J Med Chem* 50:455-461.

Yun C H, Kim K H, Kim D H, Jung H C and Pan J G (2007) The bacterial P450 BM3: a prototype for a biocatalyst with human P450 activities. *Trends Biotechnol* 25:289-298.

The invention claimed is:

1. A method for preparing piceatannol, the method comprising reacting at least one mutant of CYP102A1 with resveratrol, wherein CYP102A1 is a cytochrome P450 from *B. megaterium*, wherein the mutant of CYP102A1 comprises an amino acid sequence at least 95% identical to SEQ ID NO: 16, wherein the amino acid sequence of the mutant of CYP102A1 differs from SEQ ID NO: 16 by one or more amino acid substitutions at positions 47, 51, 64, 74, 81, 86, 87, 143, 188 and/or 267 of SEQ ID NO: 16, wherein the mutant of CYP102A1 catalyzes the conversion of resveratrol to piceatannol, and wherein the one or more substitutions are selected from the group consisting of:
  substitution of the amino acid corresponding to arginine at position 47 of SEQ ID NO: 16 with one amino acid selected from the group consisting of alanine, valine, leucine, isoleucine, proline, methionine, phenylalanine, and tryptophan,
  substitution of the amino acid corresponding to tyrosine at position 51 of SEQ ID NO: 16 with one amino acid selected from the group consisting of phenylalanine, alanine, valine, leucine, isoleucine, proline, methionine, and tryptophan,
  substitution of the amino acid corresponding to glutamic acid at position 64 of SEQ ID NO: 16 with one amino acid selected from the group consisting of glycine, serine, threonine, cysteine, tyrosine, asparagine, and glutamine,
  substitution of the amino acid corresponding to alanine at position 74 of SEQ ID NO: 16 with one amino acid selected from the group consisting of glycine, serine, threonine, cysteine, tyrosine, asparagine, and glutamine,
  substitution of the amino acid corresponding to phenylalanine at position 81 of SEQ ID NO: 16 with one amino acid selected from the group consisting of alanine, valine, leucine, isoleucine, proline, methionine, and tryptophan,
  substitution of the amino acid corresponding to leucine at position 86 of SEQ ID NO: 16 with one amino acid selected from the group consisting of alanine, valine, isoleucine, proline, methionine, phenylalanine, and tryptophan,
  substitution of the amino acid corresponding to phenylalanine at position 87 of SEQ ID NO: 16 with one amino acid selected from the group consisting of alanine, valine, leucine, isoleucine, proline, methionine, and tryptophan,
  substitution of the amino acid corresponding to glutamic acid at position 143 of SEQ ID NO: 16 with one amino acid selected from the group consisting of glycine, serine, threonine, cysteine, tyrosine, asparagine, and glutamine,
  substitution of the amino acid corresponding to leucine at position 188 of SEQ ID NO: 16 with one amino acid selected from the group consisting of glycine, serine, threonine, cysteine, tyrosine, asparagine, and glutamine, and
  substitution of the amino acid corresponding to glutamic acid at position 267 of SEQ ID NO: 16 with one amino acid selected from the group consisting of alanine, valine, leucine, isoleucine, proline, methionine, phenylalanine, and tryptophan.

2. The method of claim 1, further comprising adding an NADPH-generating system.

3. The method of claim 2, wherein the NADPH-generating system comprises glucose 6-phosphate dehydrogenase, NADP$^+$, and yeast glucose 6-phosphate.

4. The method of claim 1, wherein the resveratrol is trans-resveratrol.

5. The method of claim 1, wherein the one or more substitutions are selected from the group consisting of:
  substitution of the amino acid corresponding to arginine at position 47 of SEQ ID NO: 16 with leucine (L),
  substitution of the amino acid corresponding to tyrosine at position 51 of SEQ ID NO: 16 with phenylalanine (F),
  substitution of the amino acid corresponding to glutamic acid at position 64 of SEQ ID NO: 16 with glycine (G),
  substitution of the amino acid corresponding to alanine at position 74 of SEQ ID NO: 16 with glycine (G),
  substitution of the amino acid corresponding to phenylalanine at position 81 of SEQ ID NO: 16 with isoleucine (I),
  substitution of the amino acid corresponding to leucine at position 86 of SEQ ID NO: 16 with isoleucine (I),
  substitution of the amino acid corresponding to phenylalanine at position 87 of SEQ ID NO: 16 with valine (V),
  substitution of the amino acid corresponding to glutamic acid at position 143 of SEQ ID NO: 16 with glycine (G),
  substitution of the amino acid corresponding to leucine at position 188 of SEQ ID NO: 16 with glutamine (Q), and
  substitution of the amino acid corresponding to glutamic acid at position 267 of SEQ ID NO: 16 with valine (V).

6. The method of claim 1, wherein the mutant of CYP102A1 comprises amino acid substitutions that correspond to amino acid substitutions in the CYP102A1 of SEQ ID NO: 16, wherein said substitutions are selected from the group consisting of F87A, R47L/Y51F, A74G/F87V/L188Q, R47L/L86I/L188Q, R47L/F87V/L188Q, R47L/F87V/L188Q/E267V, R47L/L86I/L188Q/E267V, R47L/L86I/F87V/L188Q, R47L/F87V/E143G/L188Q/E267V, R47L/E64G/F87V/E143G/L188Q/E267V, R47L/F81I/F87V/E143G/L188Q/E267V, and R47L/E64G/F81I/F87V/E143G/L188Q/E267V.

7. The method of claim 1, wherein the reacting step selectively produces piceatannol without producing other hydroxylated products.

8. The method of claim 1, wherein the method is carried out in an in vitro system and metabolites produced by the reaction do not inactivate the mutants of CYP102A1.

9. A method for making piceatannol from resveratrol, the method comprising the steps of:
  providing a catalyst comprising a mutant of CYP102A1, wherein CYP102A1 is a cytochrome P450 from *B. megaterium*; and reacting resveratrol in the presence of the catalyst and an NADPH-generating system; wherein the reacting step selectively produces one major metabolite that is piceatannol, wherein the mutant of CYP102A1 comprises an amino acid sequence at least 95% identical to SEQ ID NO: 16, wherein the amino acid sequence of the mutant of CYP102A1 differs from SEQ ID NO: 16 by one or more amino acid substitutions at positions 47, 51, 64, 74, 81, 86, 87, 143, 188 and/or 267 of SEQ ID NO: 16, wherein the mutant of CYP102A1 catalyzes the conversion of resveratrol to piceatannol, and wherein the one or more substitutions are selected from the group consisting of:

substitution of the amino acid corresponding to arginine at position 47 of SEQ ID NO: 16 with one amino acid selected from the group consisting of alanine, valine, leucine, isoleucine, proline, methionine, phenylalanine, and tryptophan, substitution of the amino acid corresponding to tyrosine at position 51 of SEQ ID NO: 16 with one amino acid selected from the group consisting of phenylalanine, alanine, valine, leucine, isoleucine, proline, methionine, and tryptophan, substitution of the amino acid corresponding to glutamic acid at position 64 of SEQ ID NO: 16 with one amino acid selected from the group consisting of glycine, serine, threonine, cysteine, tyrosine, asparagine, and glutamine, substitution of the amino acid corresponding to alanine at position 74 of SEQ ID NO: 16 with one amino acid selected from the group consisting of glycine, serine, threonine, cysteine, tyrosine, asparagine, and glutamine, substitution of the amino acid corresponding to phenylalanine at position 81 of SEQ ID NO: 16 with one amino acid selected from the group consisting of alanine, valine, leucine, isoleucine, proline, methionine, and tryptophan, substitution of the amino acid corresponding to leucine at position 86 of SEQ ID NO: 16 with one amino acid selected from the group consisting of alanine, valine, isoleucine, proline, methionine, phenylalanine, and tryptophan, substitution of the amino acid corresponding to phenylalanine at position 87 of SEQ ID NO: 16 with one amino acid selected from the group consisting of alanine, valine, leucine, isoleucine, proline, methionine, and tryptophan, substitution of the amino acid corresponding to glutamic acid at position 143 of SEQ ID NO: 16 with one amino acid selected from the group consisting of glycine, serine, threonine, cysteine, tyrosine, asparagine, and glutamine, substitution of the amino acid corresponding to leucine at position 188 of SEQ ID NO: 16 with one amino acid selected from the group consisting of glycine, serine, threonine, cysteine, tyrosine, asparagine, and glutamine, and substitution of the amino acid corresponding to glutamic acid at position 267 of SEQ ID NO: 16 with one amino acid selected from the group consisting of alanine, valine, leucine, isoleucine, proline, methionine, phenylalanine, and tryptophan.

10. The method of claim 9, wherein the resveratrol is trans-resveratrol.

11. The method of claim 9, wherein the CYP102A1 comprises SEQ ID NO: 16.

12. The method of claim 9, wherein the one or more substitutions are selected from the group consisting of:
substitution of the amino acid corresponding to arginine at position 47 of SEQ ID NO: 16 with leucine (L),
substitution of the amino acid corresponding to tyrosine at position 51 of SEQ ID NO: 16 with phenylalanine (F),
substitution of the amino acid corresponding to glutamic acid at position 64 of SEQ ID NO: 16 with glycine (G),
substitution of the amino acid corresponding to alanine at position 74 of SEQ ID NO: 16 with glycine (G),
substitution of the amino acid corresponding to phenylalanine at position 81 of SEQ ID NO: 16 with isoleucine (I),
substitution of the amino acid corresponding to leucine at position 86 of SEQ ID NO: 16 with isoleucine (I),
substitution of the amino acid corresponding to phenylalanine at position 87 of SEQ ID NO: 16 with valine (V),
substitution of the amino acid corresponding to glutamic acid at position 143 of SEQ ID NO: 16 with glycine (G),
substitution of the amino acid corresponding to leucine at position 188 of SEQ ID NO: 16 with glutamine (Q), and
substitution of the amino acid corresponding to glutamic acid at position 267 of SEQ ID NO: 16 with valine (V).

13. The method of claim 9, wherein the mutant of CYP102A1 comprises amino acid substitutions that correspond to amino acid substitutions in the CYP102A1 of SEQ ID NO: 16, wherein said substitutions are selected from the group consisting of F87A, R47L/Y51F, A74G/F87V/L188Q, R47L/L86I/L188Q, R47L/F87V/L188Q, R47L/F87V/L188Q/E267V, R47L/L86I/L188Q/E267V, R47L/L86I/F87V/L188Q, R47L/F87V/E143G/L188Q/E267V, R47L/E64G/F87V/E143G/L188Q/E267V, R47L/F81I/F87V/E143G/L188Q/E267V, and R47L/E64G/F81I/F87V/E143G/L188Q/E267V.

14. The method of claim 9, wherein the mutant of CYP102A1 comprises amino acid substitutions that correspond to amino acid substitutions in the CYP102A1 of SEQ ID NO: 16, wherein said substitutions are selected from the group consisting of A74G/F87V/L1188Q, R47L/L86I/L188Q, R47L/F87V/L188Q, R47L/F87V/L188Q/E267V, R47L/L86I/L188Q/E267V, R47L/L86I/F87V/L188Q, R47L/F87V/E143G/L188Q/E267V, R47L/E64G/F87V/E143G/L188Q/E267V, R47L/F81I/F87V/E143G/L188Q/E267V, and R47L/E64G/F81I/F87V/E143G/L188Q/E267V.

15. The method of claim 9, wherein said method is carried out in an in vitro system and wherein metabolites generated by the reaction do not inactivate the catalyst.

* * * * *

SEQUENCE LISTING

```
<160> NUMBER OF SEQ ID NOS: 16

<210> SEQ ID NO 1
<211> LENGTH: 31
<212> TYPE: DNA
<213> ORGANISM: Artificial Sequence
<220> FEATURE:
<223> OTHER INFORMATION: Synthetic construct: primer

<400> SEQUENCE: 1
agcggatcca tgacaattaa agaaatgcct c                                    31

<210> SEQ ID NO 2
<211> LENGTH: 20
<212> TYPE: DNA
<213> ORGANISM: Artificial Sequence
<220> FEATURE:
<223> OTHER INFORMATION: Synthetic construct: primer

<400> SEQUENCE: 2
atcgagctcg tagtttgtat                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic construct: primer

<400> SEQUENCE: 3
gcgcctggtc tggtaacgcg                                                 20

<210> SEQ ID NO 4
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 4
gtaacgcgct tcttatcaag t                                               21

<210> SEQ ID NO 5
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 5
gcatgcgatg gctcacgctt t                                               21

<210> SEQ ID NO 6
<211> LENGTH: 25
```

```
<212> TYPE: DNA
<213> ORGANISM: Artificial Sequence
<220> FEATURE:
<223> OTHER INFORMATION: Synthetic construct: primer

<400> SEQUENCE: 6
taagtcaagg ccttaaattt gtacg                                    25

<210> SEQ ID NO 7
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 7
gtacgtgata ttgcaggaga c                                        21

<210> SEQ ID NO 8
<211> LENGTH: 22
<212> TYPE: DNA
<213> ORGANISM: Artificial Sequence
<220> FEATURE:
<223> OTHER INFORMATION: Synthetic construct: primer

<400> SEQUENCE: 8
ggagacggga ttttacaag ct                                        22

<210> SEQ ID NO 9
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 9
gacgggttag cgacaagctg g                                        21

<210> SEQ ID NO 10
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 10
gacgggttag tgacaagctg g                                        21

<210> SEQ ID NO 11
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 11
gaagtaccgg gcgacatgac a                                        21

<210> SEQ ID NO 12
<211> LENGTH: 22
<212> TYPE: DNA
<213> ORGANISM: Artificial Sequence
<220> FEATURE:
<223> OTHER INFORMATION: Synthetic construct: primer

<400> SEQUENCE: 12
```

-continued

```
atgaacaagc agcagcgagc aa                                              22
```

<210> SEQ ID NO 13
<211> LENGTH: 21
<212> TYPE: DNA
<213> ORGANISM: Artificial Sequence
<220> FEATURE:
<223> OTHER INFORMATION: Synthetic construct: primer

<400> SEQUENCE: 13

```
ttcttaattg ggggacacgt g                                               21
```

<210> SEQ ID NO 14
<211> LENGTH: 22
<212> TYPE: DNA
<213> ORGANISM: Artificial Sequence
<220> FEATURE:
<223> OTHER INFORMATION: Synthetic construct: primer

<400> SEQUENCE: 14

```
tgcgggacac gtgacaacaa gt                                              22
```

<210> SEQ ID NO 15
<211> LENGTH: 23
<212> TYPE: DNA
<213> ORGANISM: Artificial Sequence
<220> FEATURE:
<223> OTHER INFORMATION: Synthetic construct: primer

<400> SEQUENCE: 15

```
ggagacggga ttgtgacaag ctg                                             23
```

<210> SEQ ID NO 16
<211> LENGTH: 1048
<212> TYPE: PRT
<213> ORGANISM: Bacillus megaterium

<400> SEQUENCE: 16

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175
```

```
Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
            195                 200                 205

Ile Lys Val Met Asn Asp Leu Val Asp Lys Ile Ile Ala Asp Arg Lys
            210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
            245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
            275                 280                 285

Lys Ala Ala Glu Glu Ala Ala Arg Val Leu Val Asp Pro Val Pro Ser
            290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
            325                 330                 335

Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
            355                 360                 365

Asp Asp Val Glu Glu Phe Arg Pro Glu Arg Phe Glu Asn Pro Ser Ala
370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
            405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
            435                 440                 445

Lys Ser Lys Lys Ile Pro Leu Gly Gly Ile Pro Ser Pro Ser Thr Glu
450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
            485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
            515                 520                 525

Val Leu Ile Val Thr Ala Ser Tyr Asn Gly His Pro Pro Asp Asn Ala
            530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
            565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
```

```
                595                 600                 605
    Phe Glu Gly Thr Tyr Glu Glu Trp Arg Glu His Met Trp Ser Asp Val
    610                 615                 620
    Ala Ala Tyr Phe Asn Leu Asp Ile Glu Asn Ser Glu Asp Asn Lys Ser
    625                 630                 635                 640
    Thr Leu Ser Leu Gln Phe Val Asp Ser Ala Ala Asp Met Pro Leu Ala
                        645                 650                 655
    Lys Met His Gly Ala Phe Ser Thr Asn Val Val Ala Ser Lys Glu Leu
                660                 665                 670
    Gln Gln Pro Gly Ser Ala Arg Ser Thr Arg His Leu Glu Ile Glu Leu
                675                 680                 685
    Pro Lys Glu Ala Ser Tyr Gln Glu Gly Asp His Leu Gly Val Ile Pro
    690                 695                 700
    Arg Asn Tyr Glu Gly Ile Val Asn Arg Val Thr Ala Arg Phe Gly Leu
    705                 710                 715                 720
    Asp Ala Ser Gln Gln Ile Arg Leu Glu Ala Glu Glu Lys Leu Ala
                    725                 730                 735
    His Leu Pro Leu Ala Lys Thr Val Ser Val Glu Glu Leu Leu Gln Tyr
                    740                 745                 750
    Val Glu Leu Gln Asp Pro Val Thr Arg Thr Gln Leu Arg Ala Met Ala
                755                 760                 765
    Ala Lys Thr Val Cys Pro Pro His Lys Val Glu Leu Glu Ala Leu Leu
    770                 775                 780
    Glu Lys Gln Ala Tyr Lys Glu Gln Val Leu Ala Lys Arg Leu Thr Met
    785                 790                 795                 800
    Leu Glu Leu Leu Glu Lys Tyr Pro Ala Cys Glu Met Lys Phe Ser Glu
                    805                 810                 815
    Phe Ile Ala Leu Leu Pro Ser Ile Arg Pro Arg Tyr Tyr Ser Ile Ser
                820                 825                 830
    Ser Ser Pro Arg Val Asp Glu Lys Gln Ala Ser Ile Thr Val Ser Val
                835                 840                 845
    Val Ser Gly Glu Ala Trp Ser Gly Tyr Gly Glu Tyr Lys Gly Ile Ala
    850                 855                 860
    Ser Asn Tyr Leu Ala Glu Leu Gln Glu Gly Asp Thr Ile Thr Cys Phe
    865                 870                 875                 880
    Ile Ser Thr Pro Gln Ser Glu Phe Thr Leu Pro Lys Asp Pro Glu Thr
                    885                 890                 895
    Pro Leu Ile Met Val Gly Pro Gly Thr Gly Val Ala Pro Phe Arg Gly
                900                 905                 910
    Phe Val Gln Ala Arg Lys Gln Leu Lys Glu Gln Gly Gln Ser Leu Gly
                915                 920                 925
    Glu Ala His Leu Tyr Phe Gly Cys Arg Ser Pro His Glu Asp Tyr Leu
                930                 935                 940
    Tyr Gln Glu Glu Leu Glu Asn Ala Gln Ser Glu Gly Ile Ile Thr Leu
    945                 950                 955                 960
    His Thr Ala Phe Ser Arg Met Pro Asn Gln Pro Lys Thr Tyr Val Gln
                    965                 970                 975
    His Val Met Glu Gln Asp Gly Lys Lys Leu Ile Glu Leu Leu Asp Gln
                980                 985                 990
    Gly Ala His Phe Tyr Ile Cys Gly Asp Gly Ser Gln Met Ala Pro Ala
                995                 1000                1005
    Val Glu  Ala Thr Leu Met Lys  Ser Tyr Ala Asp Val  His Gln Val
    1010                1015                1020
```

```
Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045
```